United States Patent [19]

Wolfrum et al.

[11] 4,417,964

[45] Nov. 29, 1983

[54] METHOD OF PREPARING OLEFINIC COMPOUNDS

[75] Inventors: Jürgen Wolfrum, Rosdorf; Michael Kneba, Göttingen, both of Fed. Rep. of Germany; Peter N. Clough, Belfast, Ireland

[73] Assignee: Max-Planck-Gesellschaft zur Förderung der Wissenschaften e.v., Göttigen, Fed. Rep. of Germany

[21] Appl. No.: 438,664

[22] Filed: Nov. 2, 1982

Related U.S. Application Data

[63] Continuation of Ser. No. 158,010, Jun. 9, 1980, abandoned.

[30] Foreign Application Priority Data

Sep. 21, 1979 [DE] Fed. Rep. of Germany ....... 2938353
Mar. 7, 1980 [DE] Fed. Rep. of Germany ....... 3008848

[51] Int. Cl.³ .............................................. B01J 19/12
[52] U.S. Cl. ........................... 204/158 R; 204/162 R; 204/163 R
[58] Field of Search ............... 204/158 R, 158 L, 162, 204/163

[56] References Cited

U.S. PATENT DOCUMENTS 4,124,466 11/1978 Morrey ......................... 204/158 L Primary Examiner—Howard S. Williams
Attorney, Agent, or Firm—Felfe & Lynch

[57] ABSTRACT

A method of preparing compounds having at least one olefinic double bond, which method comprises irradiating the corresponding saturated halogenated compound in gaseous form, with pulsed coherent light or incoherent light, adjusting the wavelength of the irradiated light and the pressure and temperature conditions so that a captured cross-section of $10^{-15}$ to $10^{-25}$ cm² per molecule results, to split off hydrogen halide from said corresponding saturated compound yielding said olefinic compound.

20 Claims, 3 Drawing Figures

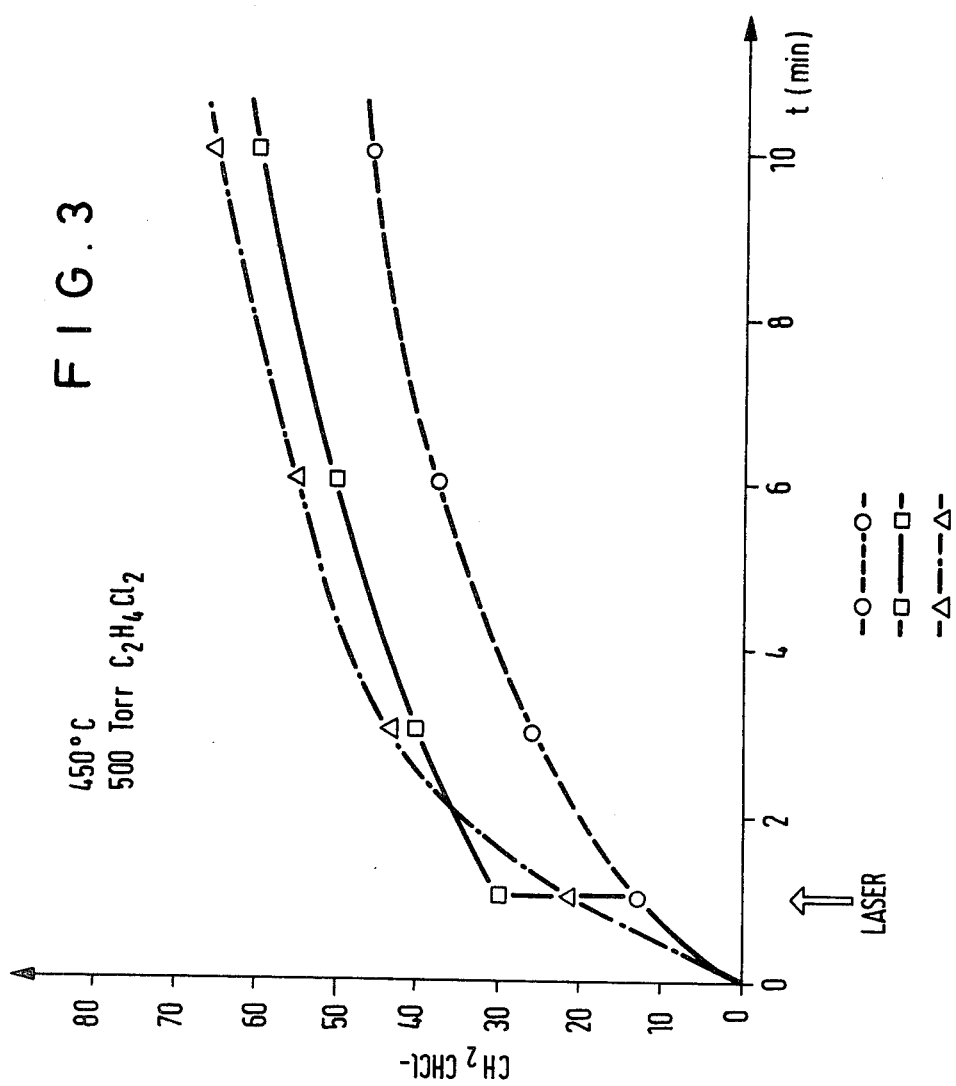

METHOD OF PREPARING OLEFINIC COMPOUNDS

This is a continuation of Ser. No. 158,010, filed June 9, 1980, now abandoned.

This invention relates to a method of preparing compounds having at least one olefinic double bond by the splitting off of hydrogen halide from the corresponding saturated compound by a radical chain reaction. The compounds which may be prepared by the present invention are optionally halogenated.

It is known that many chemical reactions take place both in the gas phase and in the liquid phase in the form of a so-called chain reaction. A chain reaction is obtained when a large number of molecules is reacted as a result of a single activating step.

If stable starting products are written as $A_1, A_2 \ldots$, and end products as $B_1, B_2 \ldots$, and active intermediates as $X_1, X_2 \ldots$, the following general scheme applies:

| (a) | $A_1 \rightarrow X_1 + B_1$ | Beginning of chain |
|---|---|---|
| (b) | $X_1 + A_2 \rightarrow B_2 + X_2$ | Continuation of chain |
| (c) | $X_2 + A_3 \rightarrow B_3 + nX_1$ | Continuation of chain (for $n > 1$ with branching chain) |

Since the cycles (b) and (c) fundamentally can be repeated any number of times, the sequence of the reaction is performed whenever an active particle $X_1$ enters the reaction, until the particle $X_1$ is finally exhausted after a reaction and is not regenerated. The number of steps (b) and (c) that take place for each introduced particle $X_1$ is taken as the chain length. It can amount to several powers of ten.

In the technical processes principally used, in which chain reactions are important, the active particles $X_1$ are introduced into the course of the reaction mostly thermally, i.e., by unspecific heating (known as "pyrolysis"). For this purpose relatively high temperatures are generally required. The high temperatures needed for the pyrolysis require a large expenditure of energy and also frequently result in undesired secondary reactions. The main part of the energy is consumed by the thermal processes in the cleavage of the reactants, and therefore in the release of the active particles, i.e., for the chain-starting reaction. The reactions (b) and (c) which continue the chain and amount to the far greater part of the total transformation, depending on the chain length, are generally sufficiently rapid at considerably lower temperatures than those required for the pyrolysis. From this it is apparent that an efficient method of preparing the active particles $X_1$ at comparatively low temperatures would offer considerable advantages.

It is known to produce such active particles, for example by the use of additives which thermally release active particles $X_1$ with relative ease. An example is the addition of $Cl_2$ (generally $X_2$) when $X_1$ is a free chlorine atom. Such additives, however, frequently entail disadvantages, such as additional cost and, for example, corrosion problems. Other known methods produce the radicals $X_1$ by photolysis with conventional light sources, such as high pressure mercury lamps. These light sources, however, make only relatively poor use of their input energy in transforming it to photon energy that can be used in the desired process. Furthermore, these light sources supply a relatively low photon density within a narrow spectral range.

The difficulties explained above are especially apparent in the preparation of compounds having one or more olefinic double bonds by the splitting off of hydrogen halide from the corresponding saturated compound containing halogen and hydrogen. The olefinically unsaturated compound obtained can also contain one or more additional halogen atoms. A typical example is the preparation of monomeric vinyl chloride (VCM) from dichloroethane.

In this process performed on a large technical scale, 1,2-dichloroethane is cleaved at about 500° C. in a pyrolysis oven several hundred meters long to vinyl chloride and hydrogen chloride. Most of the reaction involves the simple homogeneous splitting off of hydrogen chloride from dichloroethane. On account of the high reaction temperature that is required, not only are large amounts of heat required, but also a number of undesired by-products are produced which interfere with the continuation of the process and therefore they have to be separated by complicated methods.

Under the above-described conditions, the transformation amounts to about 50 to 60% and the selectivity to 96 to 99% (cf. Hydrocarbon Processing, March 1979, pp. 75–88).

THE INVENTION

The invention therefore has the object of creating a process of the kind mentioned in the beginning, in which the energy required for the achievement of the radical chain reaction is reduced, transformation and selectivity are increased, virtually no undesired by-products are formed, catalysts tending to become inactivated or poisoned are not required, and the length of time required for the reaction is shortened.

These objects are achieved in accordance with the invention by a method for the preparation of compounds, which may be halogenated if desired, having at least one olefinic double bond by the splitting off of hydrogen halide from the corresponding saturated compound containing halogen and hydrogen, which is characterized in that the gaseous saturated compound is irradiated in a reaction chamber with pulsed coherent light and/or incoherent light, and the wavelength of the light and the pressure and temperature conditions in the reaction chamber are sleected such that a capture cross section results of $10^{-15}$ to $10^{-25}$ cm$^2$ per molecule.

BRIEF DESCRIPTION OF THE DRAWINGS

FIG. 3 is a graphic representation of the VCM yield improvement with the inventive processes.

DESCRIPTION OF THE PREFERRED EMBODIMENTS

Figure 1:
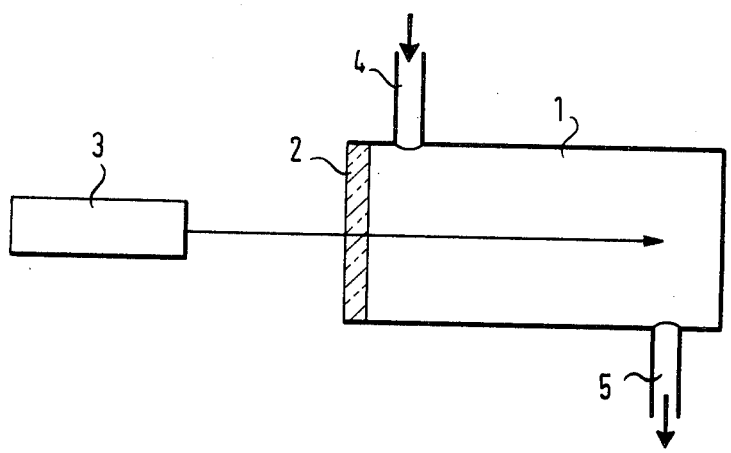
FIG. 1 shows an apparatus in which energy in the form of heat can be supplied to the starting material.

According to a first embodiment of the method of the invention the use of coherent light (a laser) is essential. This makes it possible to achieve a very high photon density and a high efficiency, and to produce monochromatic light of very sharply defined wavelength. In addition, the possibility exists of obtaining brief light pulses of high power. These properties of the coherent laser light sources permit a selective and effective production of active particles $X_1$ (as described above)

under conditions under which this can be accomplished not at all or only to a very slight extent with conventional light sources. The high monocromaticity of laser radiation permits a very selective excitation of the substances releasing the active particles $X_1$ by the selection of suitable energy transitions (absorption lines). The high photon density of laser radiation makes it possible by laser photolysis to achieve a very high concentration of reacting active particles $X_1$ for the desired chain reaction in a very short time, in a relatively great volume and in a wide temperature and pressure range. Thus a rapid transformation by the reaction is possible. The high photon density of laser light sources does not merely permit excitation by individual photon absorption as known in connection with conventional light sources: double and multiple photon absorptions are also possible. By double and multiple photon absorption, molecules can be excited to higher energy states than in the case of the single photon absorption of light of the same wavelength. As a result of this higher excitation, the excited molecules break down more rapidly.

A second important feature of the method of the invention is that the wavelength of the laser light and the pressure and temperature conditions in the reaction chamber are selected such that the above-mentioned capture cross section of $10^{-15}$ to $10^{-25}$ cm$^2$ per molecule is obtained. In other words, according to the invention, the method is practiced at wavelengths which are only slightly absorbed by the molecules. Surprisingly, it has been found that a relatively small absorption cross section is substantially more desirable, although the largest possible absorption cross section has always been striven for in the past, on the assumption that this was the way to obtain the best energy yield.

In general it can be stated that, accordingly to the invention, a wavelength must be used for the laser light which will make it possible to irradiate the entire reaction chamber in a virtually uniform manner. This prevents the light from being entirely absorbed after passing through only a portion of the reaction chamber. This, however, is the case when the wavelength of the radiation is as close as possible to the absorption wavelength of the compound being reacted, which has been the object heretofore. According to the invention, one departs considerably from these conditions and strives for no more than a relatively slight absorption.

The introduction of an active particle $X_1$ into such a reaction system is therefore accomplished in accordance with the invention by using laser radiation to excite molecules suitable for the reaction involved, such that they decompose to form active particles $X_1$:

$$A_1 + nh\nu_{laser} \rightarrow A_1^+(\text{excited}) \rightarrow X_1 + B_1 (n=1)$$

wherein "n" represents the number of the laser quanta absorbed by each molecule of the saturated compound $A_1$ containing halogen and hydrogen. This process is referred to as "laser photolysis." The laser light source in this case is one of the numerous known laser systems both in the ultraviolet range and in the visible as well as the infrared spectral range. An excimer laser is preferred.

The wavelength of the laser radiation best used depends in the manner explained above on the spectroscopic and photochemical properties of molecule $A_1$ and on the pressure and the temperature. It can be in the vacuum-ultraviolet range, in the visible range or in the infrared range of the spectrum.

According to one special embodiment of the method of the invention, the capture cross section can also be controlled by the addition of small amounts of more highly halogenated compounds, hydrogen halide, or halogen.

By the laser photocatalysis method of the invention, a rapid, quantitative splitting off of hydrogen chloride from 1,2-dichloroethane can be accomplished at considerably lower temperatures than in a purely thermal process. The reaction also takes place largely without any undesirable secondary reactions resulting in other products than vinyl chloride and hydrogen chloride.

The reaction given as an example takes place under the conditions of laser photocatalysis approximately in accordance with the following scheme: First the initiation of the reaction chain is performed by the laser photolysis of 1,2-dichloroethane (C$_2$H$_4$Cl$_2$):

$$C_2H_4Cl_2 + nh\nu_{laser} \xrightarrow{\text{Excitation}} \quad (1)$$

$$(C_2H_4Cl_2) \text{ excited} \xrightarrow{\text{decomposition}} \text{e.g. } C_2H_4Cl + Cl$$

The free chlorine atoms produced by the laser photolysis correspond to the active particles $X_1$ in the above-given general reaction scheme, and they can now react in a chain reaction with dichloroethane with the formation of vinyl chloride:

$$C_2H_4Cl_2 + Cl \rightarrow C_2H_3Cl_2 \cdot + HCl, \quad 2.$$

while the intermediate product that first develops, $$C_2H_3Cl_2 \cdot$$

decomposes to vinyl chloride as follows:

$$C_2H_3Cl_2 \cdot \rightarrow C_2H_3Cl + Cl, \quad 3.$$

so that the free chlorine atom consumed in step (2) is simultaneously fed back into the reaction chain.

Preferably radiation of a pulse duration down to $10^{-15}$ seconds and of an energy of 0.01 to 100 Joules is used. This also applies to similar reactions taking place with other saturated starting products with the splitting off of hydrogen halide. In accordance with the invention, the term halogen is used to refer to chlorine, bromine, iodine and fluorine.

In the preparation of vinyl chloride monomer from dichloroethane, the temperature can best be 200° to 550° C., and preferably 230° to 320° C. The pressure is best between 50 and 3000 kPa, preferably 0.1 to 1 MPa. However, the process can also be performed outside of the stated ranges. For example the reaction can be performed at temperatures between 10° and 700° C. As already stated, it is preferable to use excimer lasers, including not only those in the ultraviolet range but also those operating in the visible or infrared range of the spectrum. Cl$_2$, HCl, CFCl$_3$ and CF$_2$Cl$_2$, for example, can be added to control the capture cross section. These additives increase the capture cross section and split off free chlorine atoms which act as radical chain initiators. They thus make it possible to vary the number of the reaction chains and hence also the length of the reaction chains. If, for example, a chain length of $10^4$ is desired, i.e., $10^4$ cleavages for each initiating radical, the ratio of dichloroethane to additive would amount to no more than $10^{-4}$ mol per mole of dichloroethane. 1,2-

Dichloroethane is especially suitable as starting substance, but 1,1-dichloroethane can also be used.

Laser light sources suitable for this preferred embodiment of the invention are, for example, Nd:YAG ($\lambda=265$ nm); KrF ($\lambda=249$ nm); KrCl ($\lambda=225$ nm); ArF ($\lambda=193$ nm). Examples of other suitable lasers are a dye laser in the visible spectrum or a $CO_2$ laser in the infrared range.

It has furthermore been found that, in a process of this kind, very good results are also obtained when the known thermal process (pyrolysis) is combined with the photocatalysis process. In particular, it is also possible in this manner to utilize apparatus already on hand for the thermal process in conjunction with the photocatalysis process, in an economically less expensive manner, making it possible to do without expensive new industrial construction.

According to a second embodiment of the invention, therefore, the saturated compound is treated thermally in a reaction chamber and irradiated with coherent and/or incoherent light.

The reaction conditions for this combined embodiment of the invention (e.g., pressure, temperature, rate of flow of the reactants, the additives if used) can be selected in accordance with the reaction conditions of the known thermal process and with the conditions described in connection with the first embodiment.

It is preferable in the case of the combined embodiment to operate at temperatures between 200° and 600° C., especially between 450° and 550° C.; one can operate at standard pressure or reduced pressure, but elevated pressure is preferred. A pressure of 10 to 30 at has proven particularly advantageous because it permits an improved separation of the reaction products, especially an improved separation of the hydrogen halide. The use of small capture cross sections is still further favored by the combination of the process of the invention with the thermal process.

It is preferable to use medium-pressure metal vapor lamps or low-pressure metal vapor lamps as the incoherent light sources, especially those having a quantum flux ranging from 0.01 to 10 W/cm$^2$, especially from 0.1 to 2 w/cm$^2$. Mercury, thallium and/or iron metal vapor lamps have proven desirable. The wavelengths are preferably between 250 and 350 nm. Such lamps involve substantially lower investment and operating costs than laser systems.

The thermal treatment and the radiation can take place simultaneously or in successive steps. The reactants can be at rest in the reaction chamber, but, especially when medium pressure or low pressure lamps are used, it is better for the reactants to be flowing through the reaction chamber. This is because it has been found that, when medium or low pressure lamps are used the windows rapidly become covered with by-products. This problem is not great when laser beams are used, since then the higher energy drives off the particles that have lodged on the windows. It is therefore recommendable in the case of incoherent light sources to follow a procedure in which the reactants flow at a relatively high rate past the irradiation window, so that the degradation products that form will not occur in any appreciable amount except downstream from the window. The rate of flow will especially be selected on the basis of the nature and the cross section of the reaction vessel.

In such cases it has proven especially advantageous to perform the thermal treatment and the irradiation in a step-by-step manner, some of the steps being repeatable, as for example in the following order: (a) thermal treatment and/or (b) irradiation and/or (c) thermal treatment and/or (d) irradiation. The irradiation steps can be performed alternately with coherent light and with incoherent light. The reactants therefore are, for example, first heated to the thermal treatment temperature and then run past the irradiation window. The velocity of flow is best selected such that the temperature favorable for the photochemical reaction is achieved before the reactants pass the window. Then, after the irradiation, another thermal treatment can be performed. It is possible also to install an additional laser further downstream, resulting, for example, in the following sequence: (a) thermal treatment, (b) irradiation with a low-pressure or medium-pressure lamp, (c) thermal treatment and/or (d) irradiation by laser. A laser of step (d), if preceded by the irradiation step (b), can then operate on much lower energy than in the case of a single laser irradiation step, resulting in a considerable cost saving.

If laser irradiation is used, the optimum wavelength will depend on the spectroscopic and photochemical properties of the reactants, and can be between 10 nm and 500 nm. The laser irradiation can be pulsed or continuous, i.e., it can act for between $10^{-15}$ seconds and $\infty$ seconds.

The drawing will serve for the further explanation of the invention. In the appended drawing, FIG. 1 shows an apparatus in which energy in the form of heat can first be supplied to the starting material. This apparatus consists of a reactor 1, closed off at one end by a window 2 which is transparent to the laser light. Outside of the window is the radiation source 3 whose radiation enters the reaction chamber 1 through the window 2. The substance that is to be reacted is introduced into the reaction chamber at 4 through a valve and appropriate pipes. The reactants can either flow through the reaction chamber or they can be at rest therein. A pressure gauge following the valve serves for pressure control. After the chemical reaction has taken place, the reaction mixture is withdrawn at 5 and processed.

Figure 2:
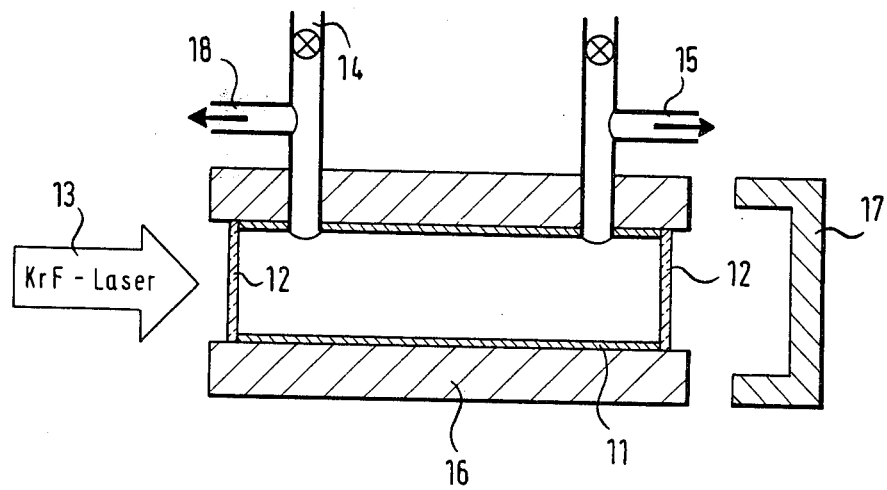
FIG. 2 shows an electrically heated quartz reactor for production of vinyl chloride monomer (VCM).

A special embodiment of the above apparatus for the production of vinyl chloride monomer (VCM) is shown in FIG. 2 of the drawing. It consists of an electrically heated quartz reactor 11 of 15×2.5 cm. The reactor is provided at its ends with quartz panes 12 through which the radiation of a KrF excimer laser 13 (wavelength 249 nm; pulse duration $10^{-8}$ seconds, pulse energy 160 mJ) enters into the reaction chamber. The dichloroethane is fed in at 14, and the reaction mixture is removed to a gas chromatograph at 15. The reaction temperature is regulated by the oven 16. A laser energy meter 17 is disposed behind the radiation outlet window. The pressure in the reactor is measured by a pressure gauge connected at 18.

FIG. 3 of the drawing is a graphic representation of the improvement of the VCM yield in relation to the number of laser pulses under the conditions given in Example 1, and by combining the thermal process with the photochemical process under the conditions given in Example 2.

An embodiment of the process of the invention that was found especially advantageous when applied to the production of VCM was the addition of oxygen or nitromethane, mixed if desired with inert gas having a partial pressure of 1 Pa to 6.5 kPa. In this manner a very great chain length can be obtained, amounting to from $10^5$ to $10^6$ transformations per excitation.

If, however, contrary to the teaching of the invention, coherent light of high capture cross section, such as for example the wavelength of the argon laser of 193 nm corresponding to the excitation wavelength of dichloroethane, fewer firings are necessary as a result of the higher energy content, but on the other hand the vinyl chloride itself can then absorb, so that unwanted polymerization reactions can occur. If, however, one operates under the conditions specified by the invention, the purity of the reaction product amounts to more than 99.9%. Even in gas chromatography, no impurities can be detected.

The process is suitable for reactions both in the gas phase and in the liquid phase. Other examples of reactions according to the invention are the preparation of:

| | |
|---|---|
| Vinyl fluoride | $C_2H_4FCl \rightarrow C_2H_3F + HCl$ |
| Tetrafluoroethylene | $C_2F_4HCl \rightarrow C_2F_4 + HCl$ |
| Chloroprene | $C_4H_7Cl_2 \rightarrow C_4H_6Cl + HCl$ |
| Propylene | $C_3H_7Cl \rightarrow C_3H_6 + HCl$ |
| Vinylidene chloride | $C_2H_3Cl_3 \rightarrow C_2H_2Cl_2 + HCl$ |

In comparison with the known method, therefore, the invention permits the performance of the desired reaction at comparatively lower temperature with considerably greater speed and without undesired secondary reactions. Since no solid phase catalysts are necessary, there is no danger of catalyst poisoning.

In comparison with the thermal process, considerable improvements of yield can be attained with the process of the invention. For example, under technical conditions, by combination with a single irradiation step using a medium-pressure lamp, yield improvements of up to 10% are obtained.

When compared with other laser photochemical processes, the process of the invention provides a utilization of the laser photons that is an order of magnitude better, due to the manifold reaction, corresponding to the reaction chain length, of the active particles produced by the laser radiation. By the combination of the laser photolysis with a chain reaction in accordance with the invention, the economy of a laser photochemical process is therefore also improved many times.

The reactors technically used in the known thermal processes can serve as the reaction vessels for the process of the invention after the installation or one or more windows for the admission of the radiation.

Additional variants in the construction of such apparatus are also possible, e.g., by the installation of additional transparent windows for the combination of several radiation sources.

The following examples will explain the invention in conjunction with the preparation of vinyl chloride monomer (VCM).

EXAMPLE 1

The temperature in the reactor was 300° C., the pressure about 70 kPa. With 20 laser pulses of a duration of $10^{-8}$ seconds and 160 mJ per pulse, a 50% transformation to VCM was achieved. Under these conditions, and with an absorption length of 15 cm, approximately 1% of the krypton fluoride laser light is absorbed, i.e., approximately $2.1 \times 10^{15}$ KrF laser photons. Under these conditions, however, $10^{19}$ vinyl chloride molecules are formed per laser pulse, i.e., at least 5000 vinyl chloride molecules are produced per laser quantum absorbed, corresponding to a radical reaction chain length of greater than 5000. No impurities can be detected in the gas chromatography. The impurities must therefore be less than 0.1%.

The consumption of energy for the production of the laser photons amounts to only 5% of the energy that is required in order to heat the dichloroethane from 300° C. to the 500° C. required for the known technical process.

EXAMPLE 2

Preparation of monomeric vinyl chloride (VCM) from 1,2-dichloroethane.

The apparatus of FIG. 2 was used. The radiation sources were (a) a laser (wavelength 308 nm, pulse energy 100 mJ) and (b) a medium pressure mercury vapor lamp (wavelength 254 nm, output 10 mW/cm$^2$). The reaction temperature in the reactor was 450° C., the pressure 500 Torr.

By the use of light source (a) as well as light source (b) a substantial increase of the transformation was achieved (cf. FIG. 3).

It will be understood that the specification and examples are illustrative, but not limitative of the present invention and that other embodiments within the spirit and scope of the invention will suggest themselves to those skilled in the art.

What is claimed is:

1. Method of preparing a compund having at least one olefinic double bond, which method comprises initiating a chain reaction by irradiating the corresponding saturated halogenated compound in gaseous form, with pulsed coherent light or incoherent light, adjusting the wavelength of the irradiated light and the pressure and temperature conditions so that a capture cross-section of $10^{-15}$ to $10^{-25}$ cm$^2$ per molecule results, to split off hydrogen halide from said corresponding saturated compound yielding said olefinic compound.

2. Method as claimed in claim 1 wherein radiation is used having a pulse duration of down to $10^{31}$ $^{15}$ seconds and an energy of 0.01 to 100 Joules.

3. Method as claimed in claim 1 wherein the capture cross-section is regulated by the addition of small amounts of more highly halogenated compounds, hydrogen halide or halogen.

4. Method as claimed in claim 1 wherein said saturated halogenated compound is dichloroethane, to produce vinyl chloride.

5. Method as claimed in claim 4 wherein a temperature from 200° C. to 600° C. is used.

6. Method as claimed in claim 5 wherein coherent light is used and a temperature of 230° C. to 350° C. is applied.

7. Method as claimed in claim 5 wherein incoherent light is used and a temperature of 450° C. to 550° C. is applied.

8. Method as claimed in claim 4 wherein a pressure of from 50 to 3000 kPa is applied.

9. Method as claimed in claim 8 wherein a pressure of from 0.1 and 1 MPa is applied.

10. Method as claimed in claim 4 wherein oxygen or nitromethane is added to the dichloroethane at a partial pressure of between 1 Pa and 6.5 kPa.

11. Method as claimed in claim 10 wherein said oxygen or nitromethane is mixed with an inert gas.

12. Method as claimed in claim 1 wherein incoherent light is used and a metal vapor medium pressure lamp or low pressure lamp is used as the incoherent light source.

13. Method as claimed in claim 12 wherein a mercury, thallium or iron metal vapor lamp is used.

14. Method as claimed in claim 12 wherein said metal vapor lamp has a quantum flux range of from 0.01 to 10 $W/cm^2$.

15. Method as claimed in claim 12 wherein said metal vapor lamp has a quantum flux range of from 0.1 to 2 $W/cm^2$.

16. Method as claimed in claim 1 wherein the reactant flows through a reaction chamber.

17. Method as claimed in claim 1 wherein said temperature conditions comprise a thermal treatment, and said thermal treatment and said irradiation are performed successively step-wise.

18. Method as claimed in claim 17 wherein one or more of said thermal treatment and irradiation steps are repeated.

19. Method as claimed in claim 18 comprising the following steps
   (a) thermal treatment;
   (b) irradiation;
   (c) thermal treatment; and
   (d) irradiation.

20. Method as claimed in claim 18 wherein successive irradiation steps operate alternately with coherent light and incoherent light.

* * * * *

UNITED STATES PATENT AND TRADEMARK OFFICE
CERTIFICATE OF CORRECTION

PATENT NO. : 4,417,964
DATED : November 29, 1983
INVENTOR(S) : Jürgen Wolfrum, et al.

It is certified that error appears in the above-identified patent and that said Letters Patent is hereby corrected as shown below:

Col. 2, line 47 "sleected" should be -- selected --.

Col. 3, line 34, "accordingly" should be -- according --.

Claim 2, line 2, "$10^{31\ 15}$" should be -- $10^{-15}$ --.

Signed and Sealed this

Twenty-fourth Day of July 1984

[SEAL]

Attest:

GERALD J. MOSSINGHOFF

Attesting Officer          Commissioner of Patents and Trademarks